United States Patent [19]

Champion et al.

[11] Patent Number: 4,734,192

[45] Date of Patent: Mar. 29, 1988

[54] MULTIWELL MEMBRANE FILTRATION APPARATUS

[75] Inventors: Helena M. Champion, Swampscott, Mass.; Joseph J. Pierog, Salem, N.H.; Joseph E. Peters, Carlisle, Mass.

[73] Assignee: Millipore Corporation, Bedford, Mass.

[21] Appl. No.: 747,687

[22] Filed: Jun. 21, 1985

Related U.S. Application Data

[63] Continuation of Ser. No. 555,421, Nov. 23, 1983, abandoned, which is a continuation of Ser. No. 394,225, Jul. 1, 1982, abandoned.

[51] Int. Cl.[4] .............................................. B01D 13/00

[52] U.S. Cl. .................................... 210/335; 210/489; 210/492; 210/321.72; 422/101

[58] Field of Search ............... 210/321, 335, 436, 472, 210/489–492, 927, 433.2; 422/101; 55/159; 555/421

[56] References Cited

U.S. PATENT DOCUMENTS

| | | | |
|---|---|---|---|
| Re. 30,562 | 3/1981 | Park | 435/296 |
| 768,605 | 8/1904 | Keller et al. | 422/101 |
| 3,158,532 | 11/1964 | Pall et al. | 210/503 X |
| 3,238,056 | 3/1966 | Pall et al. | 210/505 X |
| 3,523,408 | 8/1970 | Rosenberg | 55/159 |
| 3,649,464 | 3/1972 | Freeman | 435/284 |
| 4,154,795 | 5/1979 | Thorne | 422/102 X |
| 4,246,339 | 1/1981 | Cole et al. | 422/101 X |
| 4,276,048 | 6/1981 | Leaback | 435/291 X |
| 4,304,865 | 12/1981 | O'Brien et al. | 435/285 X |
| 4,459,139 | 7/1984 | von Reis et al. | 210/416.1 X |

OTHER PUBLICATIONS

Perry, R. H. et al., *Chemical Engineers' Handbook*, 1973, McGraw-Hill Book Co., N.Y., p. 16-5.

*Primary Examiner*—David Sadowski

*Attorney, Agent, or Firm*—Andrew T. Karnakis; Paul J. Cook

[57] ABSTRACT

A multiwell filtration apparatus for the assay of microliter quantities is provided which prevents fluid loss by capillary action and gravity flow through a microporous membrane or ultrafilter. The filtration apparatus is particularly advantageous in assays requiring maintenance of fluid within the reaction wells for substantial time periods and in small sample volume assays in the range of 100 microliter volumes.

9 Claims, 5 Drawing Figures

24 22 20 20 32 28 32 26 30 34 60 50 4 50

MULTIWELL MEMBRANE FILTRATION APPARATUS

The application is a continuation application of Ser. No. 555,421, filed Nov. 23, 1983 now abandoned, which in turn is a continuation application of Ser. No. 394,225, filed July 1, 1982, now abandoned.

FIELD OF THE INVENTION

The invention relates to laboratory apparatus useful in the assay of biological and biochemical reactants and is particularly concerned with multiwell filtration devices able to retain fluids for substantial periods of time before filtration is performed.

BACKGROUND OF THE INVENTION

Test plates for in vitro analysis which contain a multiplicity of individual wells or reaction chambers are commonly known laboratory tools. Such devices have been employed for a broad variety of purposes and assays as are exemplified by U.S. Pat. Nos. 3,649,464; 4,304,865; 4,276,048; 4,154,795; and U.S. Pat. No. Re. 30,562. Microporous membrane filters and filtration devices containing such microporous membranes have become especially useful with many of the recently developed cell and tissue culture techniques and assays - particularly those in the fields of virology and immunology.

Typically, a 96-well filtration plate is used to conduct multiple assays simultaneously some of which last several hours before filtration is actually performed. With such filtration plates, especially those containing microporous membranes, there is a well recognized and recurrent problem in that fluids in the wells tend to pass through the membrane by capillary action and gravity flow thereby causing a loss of contents from within the reaction well before the desired stage in the experimental design. Prevention of fluid loss by capillary action and gravity flow becomes especially important when living cells or tissues are being maintained or grown within the reaction wells. Under these circumstances, favorable media conditions for the cells or tissue must be maintained for hours or even days and any loss of fluid from the wells, however small, will affect the condition of the cells and influence the results of the assay. Prevention of fluid loss through the membrane in this manner is also vitally important when the assay utilizes very small sample volumes as reactants, such test samples often being less than 100 microliters in volume. The pendant drop that invariably forms on the underside of the microporous membrane due to such capillary action and gravity flow is typically about 50 microliters in volume and it is apparent that a fluid loss of such proportions must drastically affect the assay.

Nevertheless, insofar as is presently known, no filtration apparatus has been able to prevent this loss of fluid from the reaction well, particularly under small sample volume assay conditions.

SUMMARY OF THE INVENTION

A filtration apparatus for the assay of microliter quantities of biological and biochemical reactants is provided comprising a plate having a plurality of apertures open at each end, filtration means disposed across and sealed about one end of each aperture thereby forming a well with a discrete filtering area and a hydrophobic fabric disposed across and bonded adjacent to the filtering area bounded by each well. The hydrophobic fabric prevents a loss of fluid by capillary action and gravity flow from within the well in the absence of an applied differential pressure. Additionally provided are fluid collection means and a guiding projection which directs such fluid as passes through the filtration means to a predetermined location within the fluid collection means.

DESCRIPTION OF THE FIGURES

The present invention may be best understood when taken in conjunction with the accompanying drawing, in which.

DETAILED DESCRIPTION OF THE EMBODIMENTS

The invention is an improvement in filtration apparatus having at least one reaction well which typically contains a microporous membrane for the separation and retention of matter from fluids. Attached adjacent to the microporous membrane is a porous hydrophobic fabric which is situated either above or preferably below the filtering microporous membrane. This hydrophobic fabric prevents fluid loss by capillary action and gravity flow through the membrane in the absence of a vacuum force but will still allow diffusion of gases into or out the interior of each well on the plate.

Figure 1:
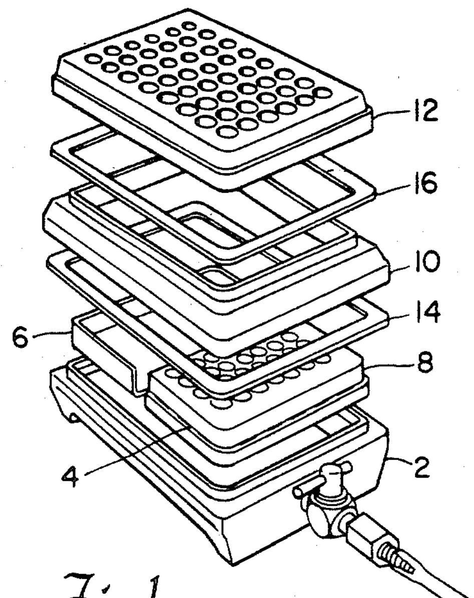
FIG. 1 is an expanded view of a vacuum assembly useful with the invention.

Embodiments of the invention are most useful with the vacuum assembly shown in FIG. 1 which is capable of simultaneously processing 96 individual test samples of up to 440 microliters (ul) each. The vacuum assembly comprises a base 2 which acts as a vacuum chamber and contains a hose barb for connection to a regulated external vacuum source. Housed within the base 2 are fluid collection means 4 which include a collection tray 6 and/or a receiving plate 8 having up to 96 individual chambers for the collection of filtrate. A filter support 10 holding a 96-well filtration plate 12 lies above the fluid collection means 4 separated by gaskets 14 and 16 which form an airtight seal in the presence of a vacuum force.

Figure 2:
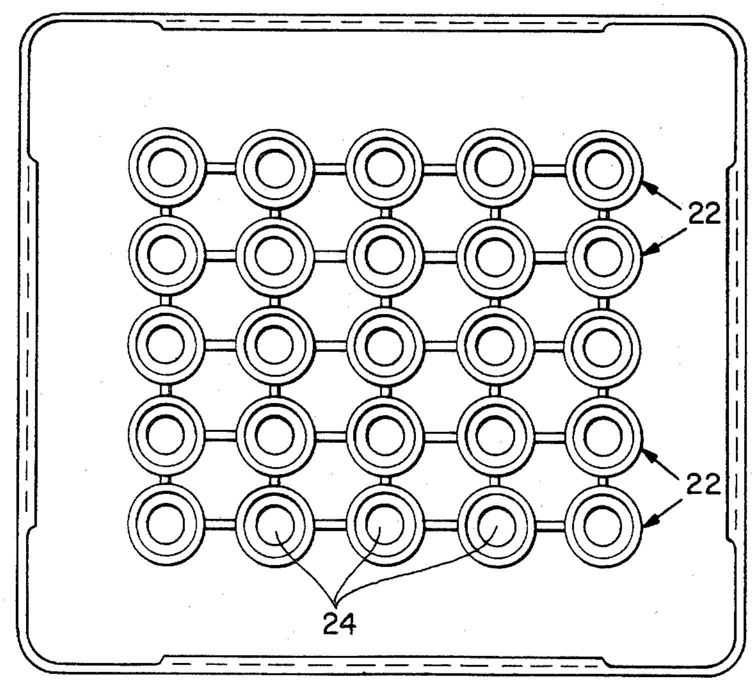
FIG. 2 is an overhead view of a filtration apparatus comprising one embodiment of the present invention.
Figure 3:
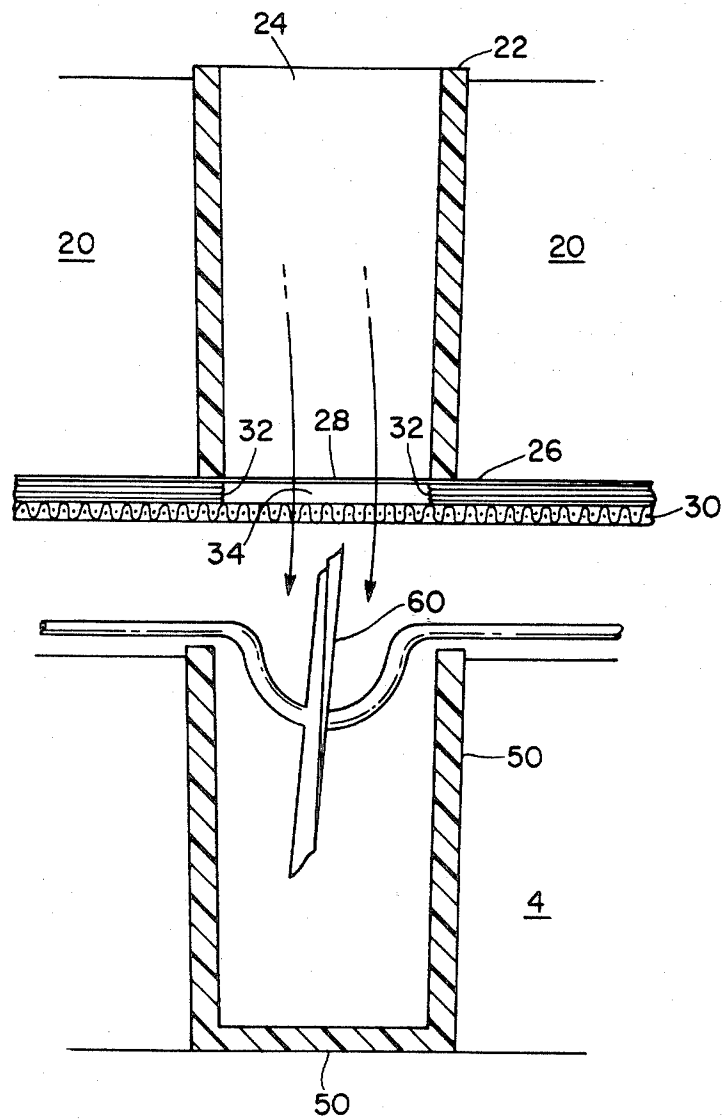
FIG. 3 is a cross-sectional view of the preferred filtration apparatus comprising the present invention.

Detailed views of the filtration plate utilizing the preferred embodiment of the present invention are shown in FIGS. 2 and 3. It will be appreciated that the number of wells found in the filtration plate are simply a matter of convenience for the investigator. The plate 20 may contain as few as one well or as many wells as are functionally permissible given the actual dimensions of the plate. The filtration plate may be formed of any resilient and nonreactive material commonly available, the composition of choice being a matter of convenience or economics only. Each well 22 comprises an aperture 24 through the entire depth of the plate, the thickness of the plate determining the volume of fluid to be retained within the well. The diameter of the aperture will vary to meet the user's needs but typically will range from 3 to 25 millimeters in diameter. The filtration means 26, typically a microporous membrane filter, is disposed across and sealed about the aperature 24 in the plate 20 such that the area across each well will serve as a filtering area 28. Methods of bonding the microporous membrane to the plate and sealing it about the perimeter of the aperature 24 are well known in the art and need not be described in detail here. The composition and flow characteristics of the filtration means 26 forming the filtering area 28 across each aperature 24 is also a matter of choice. Typically nitrocellulose membranes cellulose acetate, polycarbonate and polyvinylidene fluoride microporous membranes are selected because of their proven characteristics in aqueous solutions and tissue culture media. The porosity of the membrane will be selected with a view to the chosen application. Although 0.025 to 10.0 micrometer porosity membranes of 150 micrometers thickness are favored, the filtration means 26 are not limited to microporous membranes as such. Rather, ultrafiltration media can be utilized in lieu of microporous membrane. By the term ultrafiltration media is meant a material capable of retaining a molecule in solution. Such ultrafiltration media are useful for retaining molecules as small as about 100 daltons and generally molecules as large as about two million daltons. Examples of such ultrafiltration media are well known in the art and include polysulfone and other polymeric materials available from Millipore Corporatin under the registered trademark, PELLICON ®. Similarly, macrofiltration media such as glass fiber for retention of gross particles may be used. It will be appreciated by those ordinarily skilled in the art that the individual filtering areas 28 bounded by each well 22 can be removed via a filter punch after filtration for further processing if necessary.

As can be seen in FIG. 3, a hydrophobic fabric 30 is disposed across and bonded adjacent to the filtering areas 28 of the well 22. Preferably, the hydrophobic fabric is bonded to the filtration means abutting the well perimeter 32 such that a minute space 34 is created and maintained between the fabric 30 and the filtering area 28. The fabric 30 may be heat bondable or utilize and adhesive for attachment to the filtration means 26. In addition, the fabric 30 may be formed of woven or a nonwoven materials and be composed any of hydrophobic polyester, polyolefin, polytetrafluoroethylene or other polymer—many suitable varieties being commercially available.

It is preferred that attachment of the filtration means 26 and the hydrophobic fabric 30 to the plate 20 be performed as separate steps to insure their proper positioning and the formation of the minute space 34. Nevertheless, it is possible to attach both the filtrations means and the hydrophobic fabric simultaneously, particularly if a heat bondable hydrophobic material is used as the fabric layer.

Affixation of a porous hydrophobic fabric in this manner permits the use of small sample volumes, often less than 100 microliter (hereinafter ul), to be used as reactants. Without the fabric layer, a drop of fluid approximately 50 ul in volume will collect below the filtration means as a pendant drop and become lost. With the hydrophobic fabric in place, the pendant drop that forms below the filtering area 28 as a result of capillary action and gravity flow will be substantially retained within minute space 34 and the tendency for liquid to pass through the filtering area is subtantially reduced or entirely eliminated. As a result, assays during which the well contents require a fluid media incubation phase or a bathing of the reactants in fluid can be performed without errors or inconvenience.

Figure 4:
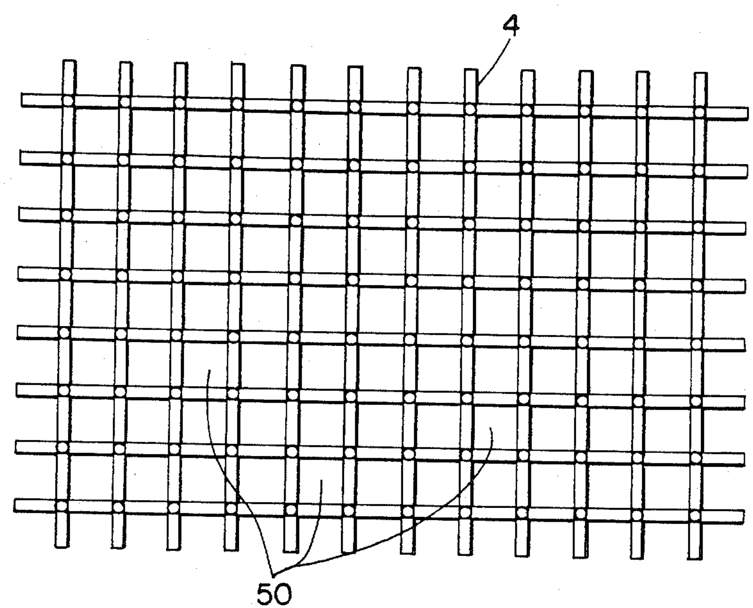
FIG. 4 is one embodiment of fluid collections means useful with the preferred embodiment illustrated in FIG. 3.
Figure 5:
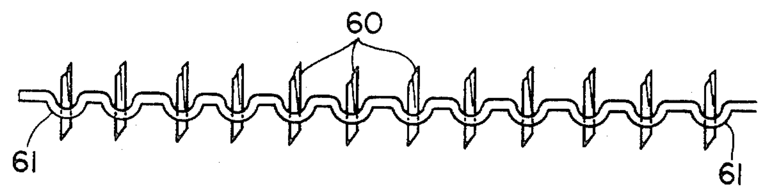
FIG. 5 is another preferred embodiment of the invention illustrated in FIG. 3.

Another aspect of the present invention is the pendant drop release fixture illustrated in FIGS. 3 and 5. This fixture is intended to be used with the multichambered fluid collection means shown in FIGS. 1 and 4 which is designed to receive filtrate from the interior of the well aligned directly above it via a plurality of individual receiving chambers 50. In this manner, the filtrate from each well will be retained separately. This compartmentalization feature alone, however, may not correct for the problem of comingling of filtrates deriving from different wells as the fluid is pulled through the hydrophobic fabric by an applied differential pressure. Similary, in those situations where the hydrophobic fabric is not present or is not necessary for the purposes of the assay, pendant drops will form and routinely collect on the underside of each filtering area. In small volume assays, the worker cannot afford to lose the 50 ul hanging as a drop from the membrane. Even in larger volume assays, an accidental movement or subsequent manipulations of the filter plate will dislodge the pendant drop and cause it to fall into the wrong receiving chamber causing cross-contamination of filtrates and erroneous test results.

Both these kinds of problems are corrected by placement of a pendant drop release fixture—in the form of a guiding projection 60—between the filtering area 28 and the fluid collection means 4 beneath the plate 20. The preferred embodiment of this guiding projection 60 appears in FIGS. 3 and 5 as a series of spikes 61 molded in a pattern corresponding to the individual filtering areas 28 in the plate 20. Each spike 60 serves a dual function: first, as a surface upon which the small volumes of fluid which would otherwise be lost as a pendant drop are collected and removed from the filtering area 28; second, as a guide by which the fluids forming a pendant drop are directed to the appropriate chamber 50 in the fluid collection means 4. The projections 61 can be injection molded or a die cut assembly. Any molding polymer material such as nylon, polystyrene, polycarbonate and polyethylene may be used for making the guiding projections; however, a hydrophilic material is preferred because it promotes interception and guidance of the pendant drop.

It is expected that the hydrophobic fabric and the fluid guiding projection will be used in tandem in the majority of assays. Nevertheless, where retention of fluid within the well is not necessary, the pendant drop release fixture may be used alone to advantage.

What we claim is:

1. A filtration apparatus able to retain liquid for extended periods of time comprising:

a plate having a thickness and a plurality of apertures extending through the thickness of the plate;

filtration means comprising a member selected from the group consisting of a microporous membrane and an ultrafiltration membrane disposed over one end of each of said apertures such that a plurality of wells each having a discrete filtering area are formed;

a hydrophobic fabric attached to said filtration means adjacent to said filtering areas and spaced apart from said filtering areas, said filtering areas and hydrophobic fabric defining spaces where liquid can be retained, said hydrophobic fabric positioned to prevent liquid placed in said wells from passing through said filtration means and said hydrophobic fabric by capillary action and gravity flow;

operably connected means for applying a differential pressure across said filtering areas and said hydrophobic fabric for effecting passage of said liquid sequentially through a said filtering area, said filtration means, a said space and said hydrophobic fabric;

a second plate defining a plurality of chambers, only one chamber being associated with each of said apertures, and operably connected means for providing that only one said chamber receives all liquid passing through the associated aperture.

2. A filtration apparatus able to retain liquid for extended periods of time comprising:

a plate having a thickness and a plurality of apertures extending through the thickness of the plate;

filtration means comprising a membrane selected from the group consisting of a microporous membrane and an ultrafiltration membrane disposed over one end of each of said apertures such that a plurality of wells each having a discrete filtering area are formed;

a hydrophobic fabric attached to said filtration means adjacent to said filtering areas and spaced apart from said filtering areas, said filtering areas and hydrophobic fabric defining spaces where liquid can be retained, said hydrophobic fabric positioned to prevent liquid placed in said wells from passing through said filtration means and said hydrophobic fabric by capillary action and gravity flow;

a second plate defining a plurality of chambers, only one chamber being associated with each of said apertures;

operably connected means for applying a differential pressure across said filtering areas and said hydrophobic fabric for effecting passage of said liquid sequentially through a said filtering area, said filtration means, a said space and said hydrophobic fabric and into a chamber; and operably connected means for providing that only one said chamber receives all liquid passing through the associated aperture including a plurality of projections each aligned with an aperture and positioned beneath said filtration means to direct liquid passing through said filtration means and said hydrophobic fabric to only one of said chambers.

3. The filtration apparatus as recited in claim 1 or 2 wherein said filtration means includes a microporous membrane.

4. The filtration apparatus as recited in claim 1 or 2 wherein said filtration means includes a microporous membrane having a pore size of at least 25 nanometers.

5. The filtration apparatus as recited in claims 1 or 2 wherein said filtration means is an ultrafiltration membrane havine a pore size which effects retention of molecules ranging in molecular weight from one hundred to two million daltons.

6. The filtration apparatus as recited in claim 1 or 2 wherein said hydrophobic fabric is selected from the group consisting of woven or nonwoven polymers.

7. The filtration apparatus as recited in claim 1 or 2 wherein said hydrophobic fabric is selected from the group consisting of polyesters, polyolefins and polytetrafluoroethylene.

8. The filtration apparatus as recited in claim 1 or 2 wherein said hydrophobic fabric is heat bondable.

9. The filtration apparatus as recited in claim 1 or 2 wherein said hydrophobic fabric is attached with adhesive.

* * * * *